(12) United States Patent
Jentzen

(10) Patent No.: US 6,231,552 B1
(45) Date of Patent: May 15, 2001

(54) THREADED LATCHING MECHANISM

(75) Inventor: S. William Jentzen, Cedar Creek, TX (US)

(73) Assignee: SAF-T-MED, Inc., Franklin Lakes, NJ (US)

( * ) Notice: Subject to any disclaimer, the term of this patent is extended or adjusted under 35 U.S.C. 154(b) by 0 days.

(21) Appl. No.: 09/305,242

(22) Filed: May 4, 1999

(51) Int. Cl.⁷ ..................................... A61M 5/00
(52) U.S. Cl. ........................... 604/241; 604/187
(58) Field of Search .................. 604/239–243, 604/232, 234, 181, 187

(56) References Cited

U.S. PATENT DOCUMENTS 5,137,509 * 8/1992 Freitas .
5,217,451 * 6/1993 Freitas .

* cited by examiner

Primary Examiner—Sharon Kennedy
Assistant Examiner—Deborah Blyveis

(57) ABSTRACT

A mechanical latching device is provided for threaded connections, such as a barrel and hub member of a medical syringe. The latching device includes an abutment and a receptacle for receipt of the abutment whereby relative movements between reciprocal members in one direction is initially terminated and subsequent movements in another direction are resisted. Movement termination in one direction and resistance in another direction may be overcome in one, or both, of the members forming the threaded connection are radially distortable to permit the members to overcome movements interference by the abutment/receptacle relationship.

3 Claims, 5 Drawing Sheets

THREADED LATCHING MECHANISM

BACKGROUND OF THE INVENTION (1) Field of the Invention

The invention pertains to a mechanical latching device for threaded connections.

(2) Brief Description of the Prior Art

A number of medical connections utilize threaded components, including syringes, intravenous tubing and catheters. Such connections are inexpensive, simple to mate and can be attached and disconnected many times. This simplicity comes with two side effects which are undesirable in certain applications. First, the presence of angled threads creates the possibility of the connection self-loosening under axial loading—a term referred to as "backdriving." The greater the angle or "pitch" of the threads, the more likely that axial loading will cause backdriving. Secondly, very little torque is often required to disassemble the connections. In the case of plastic connections which tend to "creep" or self-loosen over time, simple vibration can suffice to loosen these connections. The present invention may be used to overcome either of these shortcomings. An added advantage of the present invention is that it does not interfere with the ordinary function of the threaded connections, and requires both mating sides to incorporate the described changes to operate. Components can be manufactured incorporating the feature, and only when assembled with a mating component also incorporating the feature would the user obtain the desired benefit.

SUMMARY OF THE INVENTION

The present invention is directed to a mechanical latching device for threaded connections. The device comprises of first wall reciprocal member having an exterior thread profile thereon. A second, walled reciprocal member has an interior thread profile for mating secure engagement with the exterior thread profile. An outwardly projecting abutment has provided on one of the first and second reciprocal members. A ramped receptacle is provided for receipt of the abutment and is formed in the wall of the other of the first and second reciprocal members for terminating relative reciprocal movements between the members in one direction when the abutment is at one position in the receptacle and further thereafter resisting reciprocal movements between the members in another direction. The latching device may also include reciprocating members which are radially distortable for overcoming determination of relative reciprocal movements between the threaded connections in one direction of manipulation. The device may also be provided in a form whereby each of the threaded connection members, or one of the members, is provided in radially distortable form to overcome resistance to reciprocal movements between the members in the other direction, such as rotation in a counter-clockwise direction for unthreading, or disengaging, of the threaded members, such as a hub and barrel component of a medical syringe.

DESCRIPTION OF THE PREFERRED EMBODIMENTS

Figure 1:
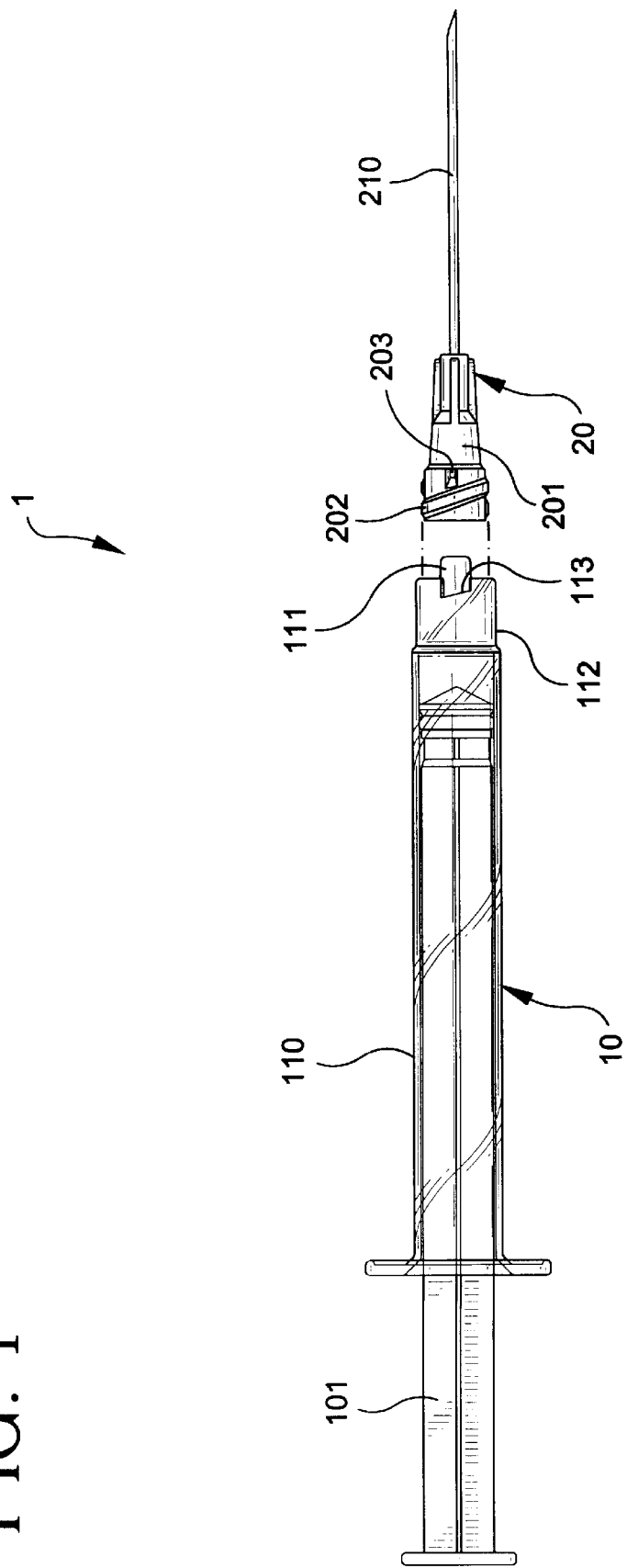
FIG. 1 is a view of the device of the present invention incorporated on a standard disposable syringe, depicted prior to assembly of the connector.

With first reference to FIG. 1, a preferred embodiment of the current invention is depicted using a disposable syringe having a barrel assembly 10 and a needle assembly 20. The barrel assembly consists of a barrel 110 for the receipt of fluid and a plunger 101 for the displacement of said fluid. As shown also in FIG. 2, the barrel component further incorporates a nozzle 111 (known in the industry as a "Luer" nozzle) and a threaded collar 112 for retaining the needle assembly 20 (known in the industry as a "Luer Lock"). Also shown in this view is an angled notch 113 extending through the collar 112.

Figure 2:
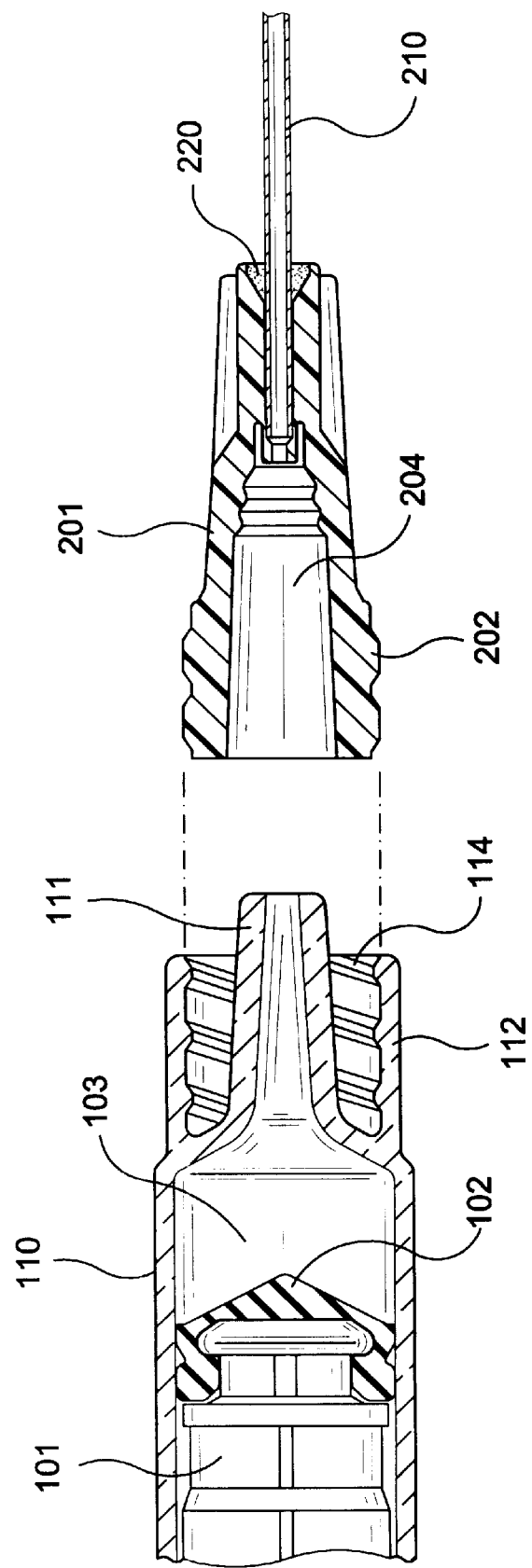
FIG. 2 is a detailed, horizontal sectional view of the medical connector incorporated in the device of FIG. 1, shown prior to assembly.

The needle assembly 20 consists of a hub 201 and a needle 210. As shown in FIG. 2, the hub has a thread 202 which mates with corresponding threads inside thread collar 112, and further incorporates a tab 203. Mating of the needle assembly 20 to the barrel assembly 10 is accomplished through application of a clockwise rotation to the needle assembly 20. Slidably positioned within the syringe barrel 110 is a plunger tip 102 affixed to plunger 101. Axial movement of the plunger 101 and plunger tip 102 within barrel 110 acts to draw medication into or expel it from the medication chamber 103.

The needle assembly contains a female socket 204 on hub 201, into which needle 210 has been affixed through the use of an adhesive 220 such as epoxy. Connection is made between these components via the tapered nozzle 111 mating with the female socket 204, and engagement of hub threads 202 with barrel collar threads 114.

Figure 3:
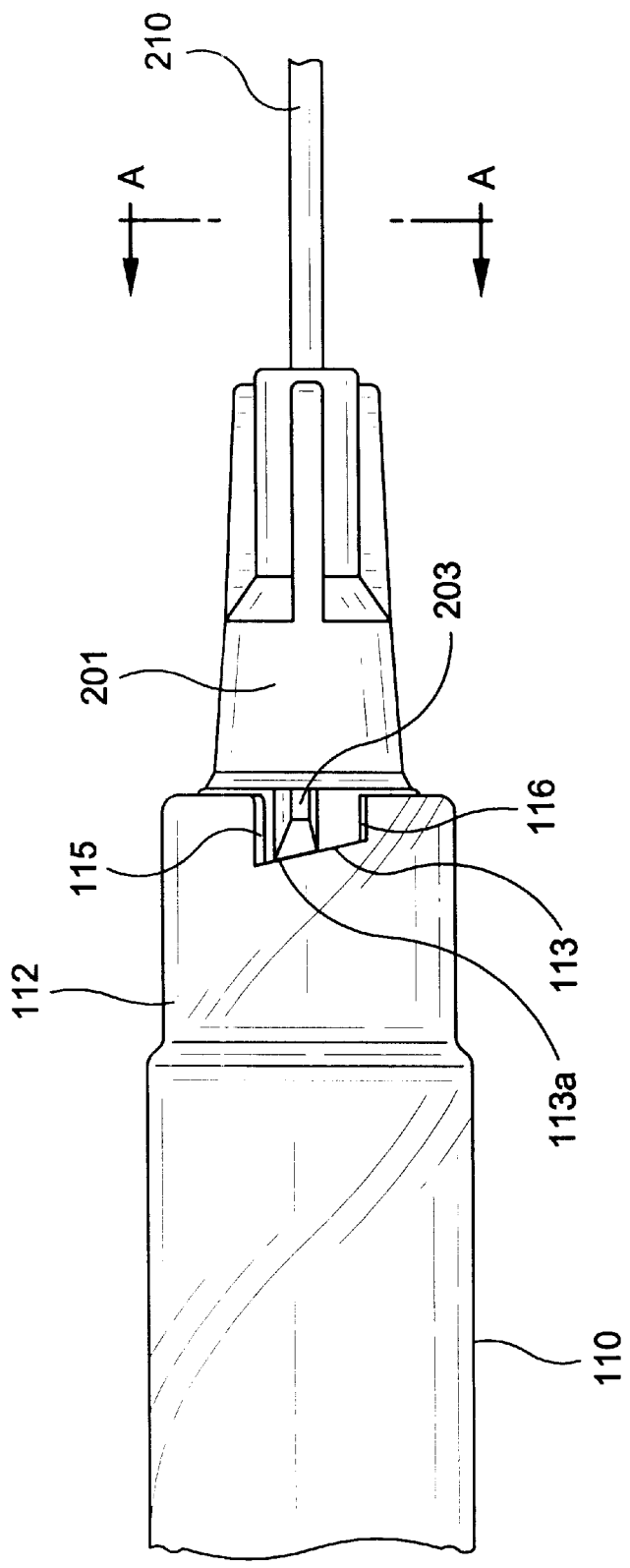
FIG. 3 is a detailed view of the connection in the device of FIG. 1, shown after assembly.

Now with reference to FIG. 3, the device of the present invention can be seen incorporated in the connection. Tab 203 on hub 201 is seated inside notch 113 on the distal end of the threaded collar 112. Over a limited range, tab 203 provides no mechanical interference with loosening or tightening of the fitting. However, tab 203 soon comes in contact with the terminal end or stop 115 of notch 113, as described below. As illustrated, notch 13 has an angled shoulder 113a which becomes steeper or more dramatic as it approaches and terminates at side 115.

Figure 4:
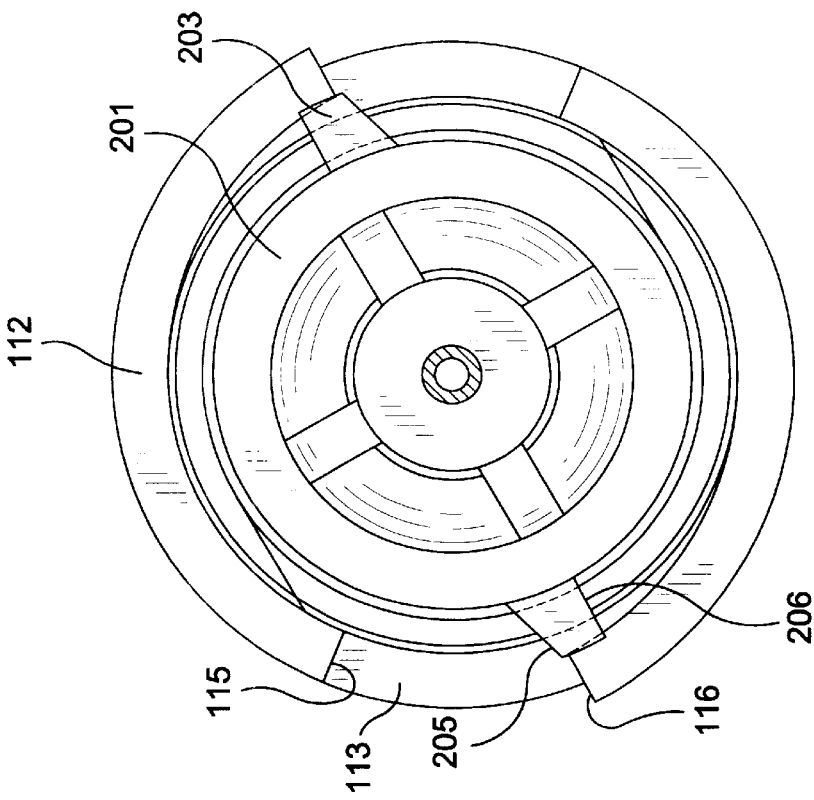
FIG. 4 is an end sectional view of the device of FIG. 3, taken along line AA and showing the completed assembly.

Taking a partial section view along line A—A in FIG. 3 results in the depiction of the features in FIG. 4. In its mated position, tab 203 sits within notch 113. Excessive tightening of the fitting causes the leading edge 205 of tab 203 to strike the assembly stop 115 of the notch 113. Initial loosening of the fitting causes the trailing edge 206 of tab 203 to contact disassembly stop 116. The size of notch 113 and tab 203, the shape of the interference between these various edges, and the materials they are composed of, can be used by the designer of the fitting to selectively establish the amount of resistance to over-tightening of the fitting, the amount of the resistance of loosening of the fitting, and the point at which these resistances are incurred during the assembly or disassembly process.

Figure 5:
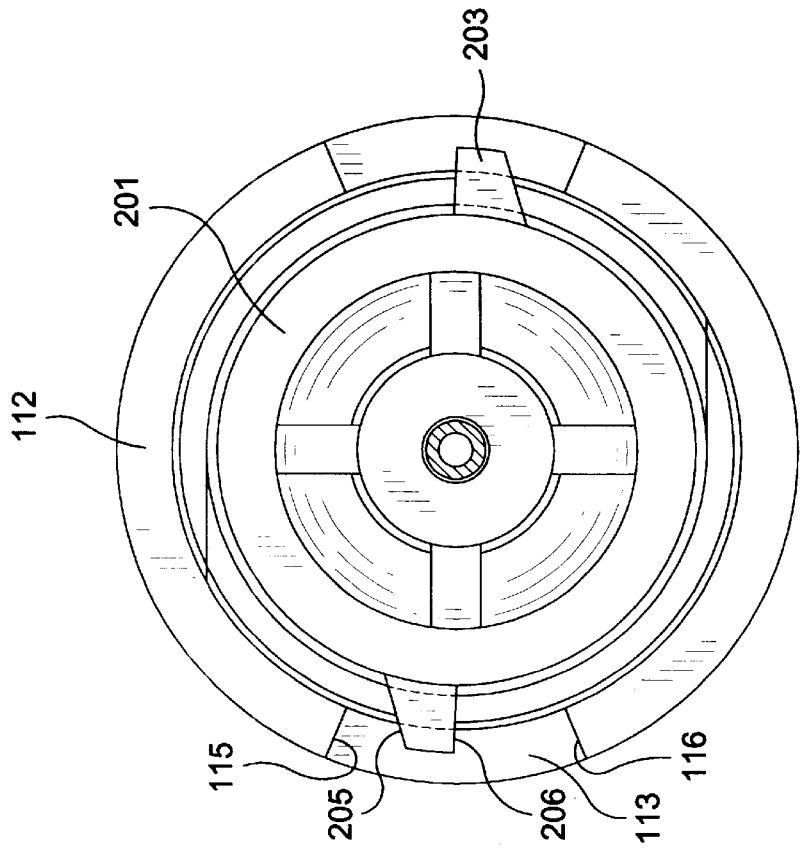
FIG. 5 is the same end sectional view depicted in FIG. 4, except the device of the present invention is shown during assembly.

FIG. 5 depicts the device of the current invention as it is being assembled (or disassembled). As assembly begins, tab leading edge 205, which is angled against the direction of rotation, first contacts the distal end of thread collar 112 at a point near the notched opening. This causes thread collar 112 to distort at that location 117—allowing the tab 203 to pass relatively easily. Once in the notch 113, the feature does not impact proper tightening of the connection.

As disassembly begins, tab trailing edge 206 first comes in contact with disassembly stop 116. The shape of this interference creates the resistance to unscrewing. In this embodiment, the interference is perpendicular to the direction of rotation—thereby requiring much greater force to continue disassembly. Indeed, if trailing edge 206 and the disassembly stop 116 met in a negative return angel, tab 203 would then "catch" thread collar end 117, maintaining its shape and preventing distortion until very large amounts of rotational force was present.

Figure 6:
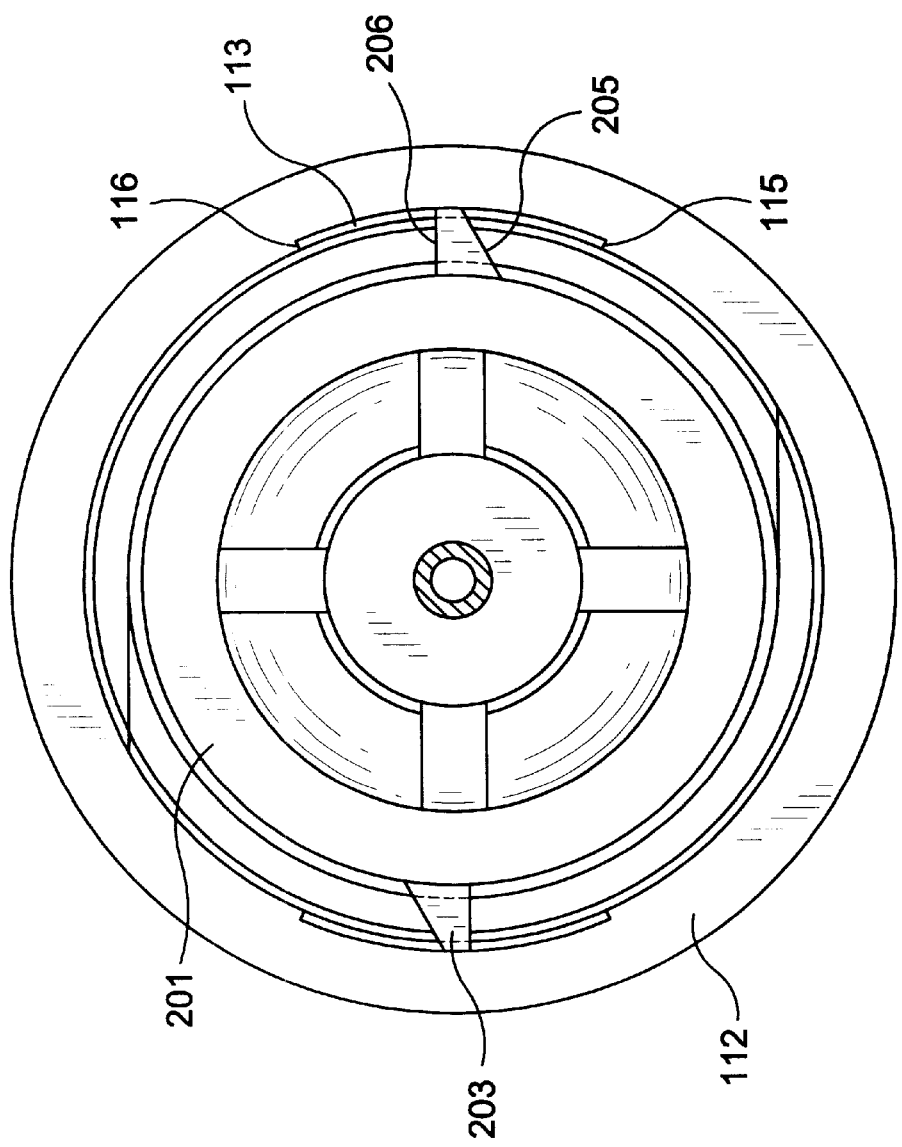
FIG. 6 is an end sectional view of an alternate preferred embodiment of the device of the present invention.

Now with respect to FIG. 6, an alternate preferred embodiment is shown where thread collar 112 has one or more notches 113 which do not extend all the way through the tread collar. Again, notch 113 has an assembly stop 115 and a disassembly stop 116. Hub 201 has a corresponding number of tabs 203, with leading edges 205 sloped to facilitate assembly and trailing edges 206 angled so as to increase disassembly torque requirements. It should be noted that, instead of elongated notches 113, a series of short notches located close to each other would provide identical assembly and disassembly force requirements, although the user would encounter a "ratcheting" feeling during assembly or disassembly.

Although the invention has been described in terms of specified embodiments which are set forth in detail, it should be understood that this is by illustration only and that the invention is not necessarily limited thereto, since other alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. A syringe for introduction or withdrawal of a liquid from a body, said syringe comprising:
    (a) a hollow needle for penetrating said body;
    (b) a hub for receiving said needle;
    (c) a syringe barrel selectively engageable to said hub and including a receptacle portion for receipt of said liquid;
    (d) an exterior thread profile on one of said hub and said barrel;
    (e) an interior thread profile on the other of said hub and said barrel for mating secure engagement with said exterior thread profile;
    (f) an outwardly projecting abutment on one of said hub and said barrel; and
    (g) a ramped receptacle for receipt of said abutment and formed in the wall of the other of said hub and barrel for terminating relative reciprocal movements between said hub and said barrel in one direction when said abutment is at one position relative to the other of said hub and said barrel, and for thereafter resisting reciprocal movements between said hub and said barrel in another direction.

2. The syringe of claim 1: at least one of said hub and said barrel being radially distortable for overcoming determination of relative reciprocal movements in said one direction.

3. The syringe of claim 1: at least one of said reciprocal members being radially distortable for overcoming said resistance between said hub and said barrel when manipulated in another direction.

* * * * *